US00PP19157P2

(12) United States Plant Patent
Dean et al.

(10) Patent No.: US PP19,157 P2
(45) Date of Patent: Aug. 26, 2008

(54) ***GERANIUM* HYBRID PLANT NAMED 'PURPLE PASSION'**

(50) Latin Name: *Geranium traversii×Geranium sessilifolia*
Varietal Denomination: Purple Passion

(76) Inventors: Mark Alston Dean, 30 Gammon Mill Road, Oropi, RD3, Tauranga (NZ); Esme Julien Dean, 30 Gamman Mill Road, Oropi, RD3, Tauranga (NZ)

( * ) Notice: Subject to any disclaimer, the term of this patent is extended or adjusted under 35 U.S.C. 154(b) by 115 days.

(21) Appl. No.: 11/704,787

(22) Filed: Feb. 9, 2007

(51) Int. Cl.
*A01H 5/00* (2006.01)

(52) U.S. Cl. ..... Plt./324
(58) Field of Classification Search ..... Plt./324, Plt./329
See application file for complete search history.

(56) References Cited

PUBLICATIONS

UpovCDROM search for cultivar Purple Passion, PBR GER015 p. 1.*

* cited by examiner

*Primary Examiner*—Annette H Para
(74) *Attorney, Agent, or Firm*—Audrey Charles

(57) ABSTRACT

A new and distinct cultivar of *Geranium* plant named 'Purple Passion', characterized by its purple-colored flowers, purple-colored foliage, and rosette growth habit.

1 Drawing Sheet

Latin name of genus and species of plant claimed: *Geranium traversii×Geranium sessilifolia.*
Variety denomination: 'Purple Passion'.

BACKGROUND OF THE INVENTION

This invention relates to a new and distinct selection of *Geranium,* a member of the Geraniaceae family. The objective of the breeding program was the development of *Geranium* hybrids with unique flower coloration, unique foliage coloration, and a rosette growth habit.

Cultivar 'Purple Passion' was discovered as a seedling in a cultivated area of a Nursery in Tauranga, New Zealand. *Geranium traversii* var. *elegans* Cockayne and *Geranium sessiliflorum* Cavanilles were grown at this Nursery and this new selection was produced by open pollination of these two species. Seed was collected off of these open pollinated plants and sown the next season. When these seedlings flowered, seedlings were selected again. This process was repeated until a final selection was made in 1993 which had large purple flowers and purple foliage.

Asexual reproduction of the new cultivar by terminal stem cuttings since 1993 at Tauranga, New Zealand has demonstrated that the new cultivar reproduces true to type with all of the characteristics, as herein described, firmly fixed and retained through successive generations of such asexual propagation.

SUMMARY OF THE INVENTION

The present invention relates to a new and distinct cultivar of *Geranium* plant botanically known as *Geranium traversii×Geranium sessilifolia* and hereinafter referred to by the cultivar name 'Purple Passion'.

The following characteristics of the new cultivar have been repeatedly observed and can be used to distinguish 'Purple Passion' as a new and distinct cultivar of *Geranium* plant:

1. Purple-colored flowers;
2. Purple-colored foliage; and
3. Rosette growth habit.

*Geranium* hybrid cultivar 'Purple Passion' combines the best horticultural traits from both parents. The rosette, bushy growth habit is typical of these two parents which are both classified in the Sessiliflorum Group. One parent, *Geranium traversii* var. *elegans* Cockayne has green foliage and light pink flowers. The other parent, *Geranium sessiliflorum* Cavanilles has bronze purplish colored foliage with white flowers. Though some seedlings exhibited a more distinct purple colored leaf, 'Purple Passion' was chosen for the large purple flowers along with the purple hue in the foliage.

Of the many commercially available *Geranium* cultivars known to the inventor, the most similar in comparison to the new cultivar is 'Pink Spice', U.S. Plant Pat. No. 12,172. However, in side by side comparisons, plants of the new cultivar differ from plants of 'Pink Spice' in the following characteristics:

1. Plants of the new cultivar have a flower color different from of 'Pink Spice'; and
2. Plants of the new cultivar have a foliage color different from plants of 'Pink Spice'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Purple Passion'. The plant illustrated was grown for approximately two years in Tauranga, New Zealand.

DETAILED BOTANICAL DESCRIPTION

Figure 1:
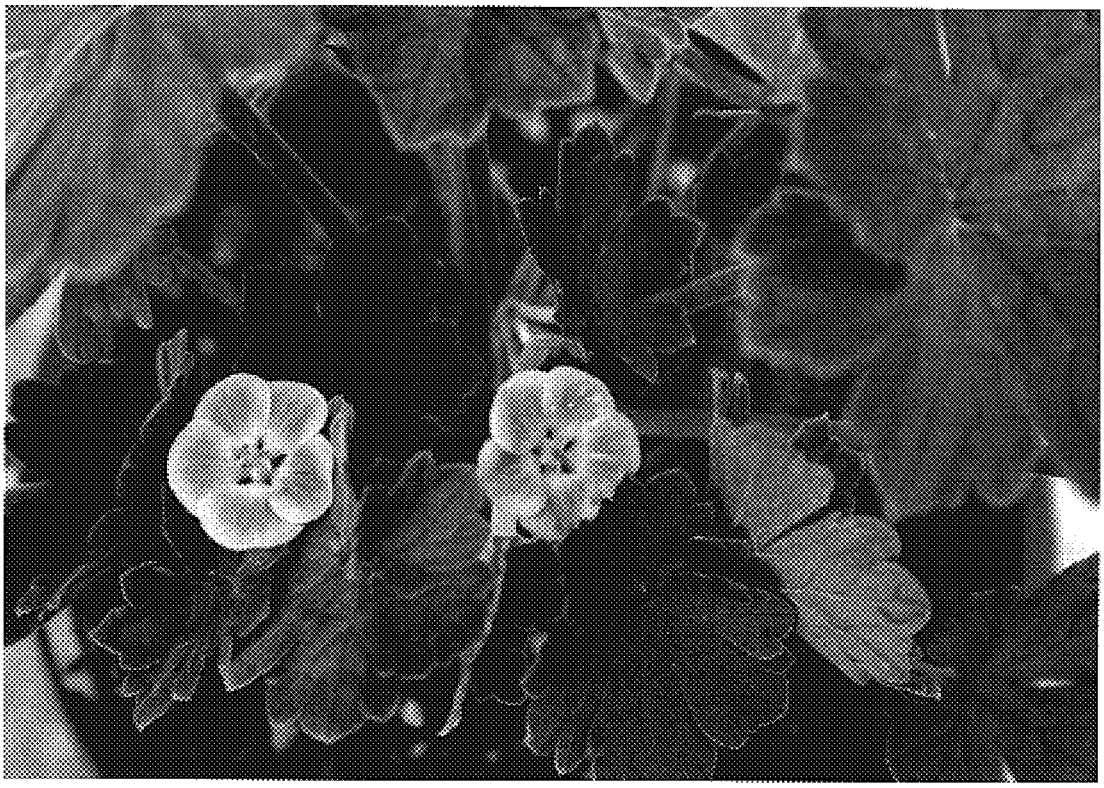
FIG. 1 illustrates the overall growth and flowering habit of 'Purple Passion'.
Figure 2:
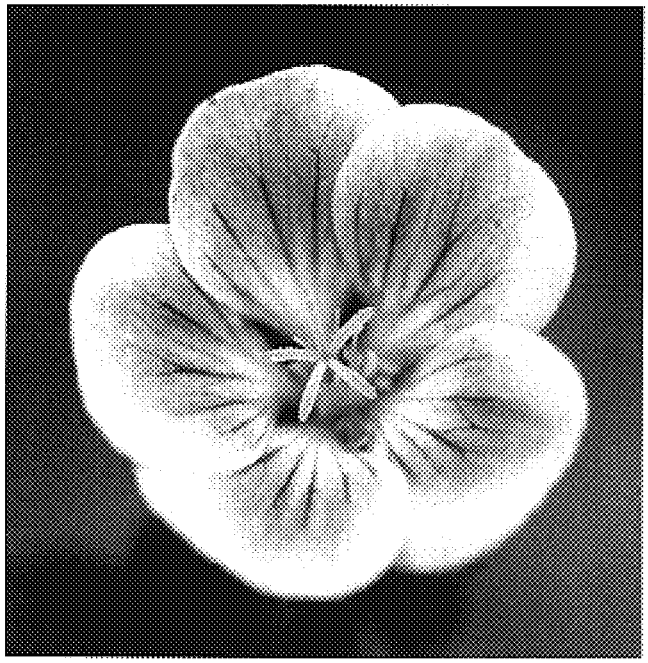
FIG. 2 illustrates a close-up view of an individual flower of 'Purple Passion'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined under natural light conditions in Tauranga, New Zealand.

The following descriptions and measurements describe plants produced from cuttings taken from stock plants and grown in a cultivated area of a Nursery in Tauranga, New Zealand. The plant size and description are based on plants grown for approximately two years in Tauranga, New Zealand.

Botanical classification: *Geranium traversii*×*Geranium sessilifolia* cultivar Purple Passion.

Parentage:

*Parents.*—*Geranium traversii* var. *elegans* Cockayne and *Geranium sessiliflorum* Cavanilles.

General plant description:

*Overall habit.*—'Purple Passion' is a low growing herbaceous perennial having a rosette growth habit with runners. Foliage surrounds the plant producing a symmetrical rounded habit. In full sun, foliage is smaller. In partial shade, larger foliage is produced. In either exposure the symmetrical rounded outline is retained. Low, spreading habit is the result of seasonal runners arising from the center of the plant and spreading in equal distance. These runners can measure up to about 60 cm to 70 cm in length in unrestricted growing areas. These runners appear in spring and die off by winter.

*Overall size.*—Height varies dependent upon climatic exposure and soil. A plant in a 15-cm wide container in full sun measures about 11 cm tall and 30 cm wide, not including runners. A plant in partial shade in unrestricted growing space measures about 25.4 cm tall and 61 cm wide. The height to width ratio is double in unrestricted growing space.

Foliage description:

*Leaves.*—Shape: Orbicular; lobed halfway down leaf blade into five to seven segments; each segment further divided by 3 shallow secondary lobes. Arrangement: Both opposite and alternate. Margins: Crenate. Length of mature leaf: Ranges from 3 cm to 6 cm. Width of mature leaf: Ranges from 5.1 cm to 8.0 cm. Texture of upper and lower surfaces: Semi-coriaceous and densely pubescent with silvery white appressed hairs giving a shiny appearance. Color of upper surface of mature foliage: N187A with venation of 187A. Color of lower surface of mature foliage: 191A with an overlay of 187B and with venation similar to lamina.

*Petiole.*—Length: Ranges from 5.1 cm to 20.3 cm. Diameter: Ranges from 2.0 mm to 3.0 mm. Texture: Pubescent. Color: 187B.

*Stipule.*—Apex: Elongated acuminate. Length: Ranges from 2.0 mm to 5.0 mm. Width: Ranges from 5.0 mm to 1.0 cm.

Flower description:

*Flowering habit.*—'Purple Passion' is freely flowering under outdoor growing conditions with substantially continuous blooming from spring through summer.

*Type.*—Single, occasionally paired, erect, funnel-shaped. Flowers are borne beneath the foliage.

*Corolla.*—Height: Ranges from 5.0 mm to 1.0 cm. Diameter: Ranges from 1.3 cm to 1.9 cm.

*Petals.*—Consistently 5 in number. Shape: Broadly spatulate. Margins: Entire, undulate, and recurved. Length: Approximately 1.0 cm. Width: Approximately 1.0 cm. Color of upper surface when fully opened: A base of 76C transitioning to N74B at center and N74D at margin.

*Calyx.*—Composed of 5 overlapping sepals. Shape: Elliptical prominent apical tip. Length: 6.0 mm. Width: 4.0 mm.

*Peduncle.*—Length: Up to 7.6 cm. Diameter: Between 1 and 2 mm. Color: 191B with a faint overlay of 187B.

*Reproductive organs.*—Androecium: Stamen quantity: 10, arranged in 2 whorls. Gynoecium: 5 lobed. Stigma: 5.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Purple Passion', substantially as herein shown and described.

* * * * *